(12) United States Patent
Tamura et al.

(10) Patent No.: US 10,640,458 B2
(45) Date of Patent: May 5, 2020

(54) PROCESS FOR PRODUCING UNSATURATED NITRILE

(71) Applicant: ASAHI KASEI KABUSHIKI KAISHA, Tokyo (JP)

(72) Inventors: Sho Tamura, Tokyo (JP); Dai Nagata, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/314,723

(22) PCT Filed: Jun. 8, 2018

(86) PCT No.: PCT/JP2018/022011
§ 371 (c)(1),
(2) Date: Jan. 2, 2019

(87) PCT Pub. No.: WO2018/225854
PCT Pub. Date: Dec. 13, 2018

(65) Prior Publication Data
US 2019/0225576 A1    Jul. 25, 2019

(30) Foreign Application Priority Data

Jun. 9, 2017 (JP) ................................ 2017-114545

(51) Int. Cl.
| C07C 253/26 | (2006.01) |
| B01J 21/08 | (2006.01) |
| B01J 23/30 | (2006.01) |
| B01J 8/18 | (2006.01) |
| B01J 35/02 | (2006.01) |
| B01J 35/00 | (2006.01) |
| B01J 23/887 | (2006.01) |

(52) U.S. Cl.
CPC ........... *C07C 253/26* (2013.01); *B01J 8/1827* (2013.01); *B01J 21/08* (2013.01); *B01J 23/30* (2013.01); *B01J 23/8876* (2013.01); *B01J 35/0026* (2013.01); *B01J 35/023* (2013.01); *B01J 35/026* (2013.01)

(58) Field of Classification Search
CPC .................................................. C07C 253/26
See application file for complete search history.

(56) References Cited

U.S. PATENT DOCUMENTS

| 5,866,708 A * | 2/1999 | Shimizu ............... C07C 253/26 |
| | | 558/320 |
| 5,965,765 A * | 10/1999 | Kurihara ............... B01J 8/1827 |
| | | 558/320 |
| 6,420,307 B1 | 7/2002 | Wu et al. |
| 7,087,551 B2 * | 8/2006 | Komada ............... B01J 23/002 |
| | | 502/211 |
| 2005/0002837 A1 | 1/2005 | Trott et al. |
| 2015/0238939 A1 | 8/2015 | Yoshida et al. |

FOREIGN PATENT DOCUMENTS

| JP | 11-349545 A | 12/1999 |
| JP | 2001-206870 A | 7/2001 |
| JP | 2002-193906 A | 7/2002 |
| JP | 2003-507180 A | 2/2003 |
| JP | 2007-503463 A | 2/2007 |
| WO | WO 2012/035881 A1 | 3/2012 |
| WO | WO 2014/051090 A1 | 4/2014 |

OTHER PUBLICATIONS

International Search Report, issued in PCT/JP2018/022011, dated Aug. 21, 2018.
International Preliminary Report on Patentability and English translation of the Written Opinion of the International Searching Authority for International Application No. PCT/JP2018/022011, dated Dec. 19, 2019.

* cited by examiner

*Primary Examiner* — Golam M Shameem
(74) *Attorney, Agent, or Firm* — Birch, Stewart, Kolasch & Birch, LLP

(57) ABSTRACT

A process for producing unsaturated nitrile, using a fluidized bed reactor having an internal space having a catalyst capable of being fluidized therein, a feed opening to feed a starting material gas comprising hydrocarbon to the internal space, and a discharge port to discharge a reaction product gas from the internal space, the process comprising a reaction step of subjecting the hydrocarbon to a vapor phase catalytic ammoxidation reaction in the presence of the catalyst in the internal space to produce the corresponding unsaturated nitrile, wherein when in the internal space, a space where an existing amount of the catalyst per unit volume is 150 kg/m$^3$ or more is defined as a dense zone and a space where an existing amount of the catalyst per unit volume is less than 150 kg/m$^3$ is defined as a sparse zone in the reaction step, a gas residence time in the sparse zone is 5 to 50 sec.

6 Claims, 1 Drawing Sheet

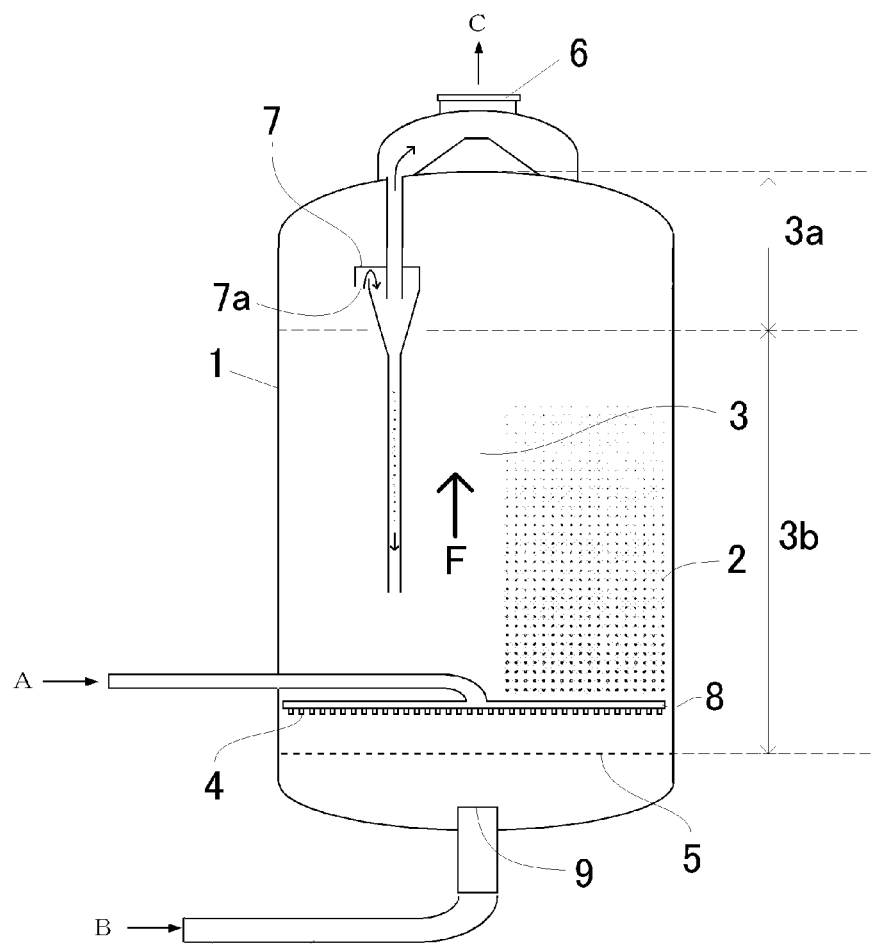

PROCESS FOR PRODUCING UNSATURATED NITRILE

TECHNICAL FIELD

The present invention relates to a process for producing unsaturated nitrile.

BACKGROUND ART

Conventionally, a fluidized bed reactor has been widely used when alkane and/or alkene is subjected to a vapor phase catalytic ammoxidation reaction in the presence of a metal composite oxide catalyst. In a fluidized bed reactor used on an industrial scale, the production operation is continuously carried out for a long period of time, and therefore, a decrease in catalytic activity exerting influence on the reaction yield, reduction of the amount of a catalyst charged due to outflow of the catalyst, and a change in particle size distribution of a catalyst or the like are brought about. On that account, for the purpose of improving a reaction yield of unsaturated nitrile, development of catalysts, improvement in internal equipment of the reactor, etc. have been made.

For example, for the purpose of providing a process for stably producing α,β-unsaturated nitrile such as acrylonitrile in a high yield over a long period of time by suppressing deterioration of a metal oxide catalyst, Patent Literature 1 discloses a vapor phase catalytic oxidation reaction method for hydrocarbon, wherein when alkane having 2 to 8 carbon atoms and/or alkene having 2 to 8 carbon atoms is subjected to a reaction of vapor phase catalytic oxidation using a fluidized bed reactor in the presence of ammonia and a metal composite oxide catalyst, the temperature of a zone where the flow density of the catalyst in the fluidized bed reactor is 50 kg/m$^3$ or less is set to be lower than the temperature of a zone where the catalyst flow density is 300 kg/m$^3$ or more.

CITATION LIST

Patent Literature

Patent Literature 1: Japanese Patent Laid-Open No. 2002-193906

SUMMARY OF INVENTION

Technical Problems

In the case where the interior of a fluidized bed reactor is divided into a dense catalyst zone and a sparse catalyst zone for convenience, the dense catalyst zone is a zone mainly purposing a reaction, and therefore, various studies have been made on the dense catalyst zone in order that the starting material gas concentration, oxygen concentration, feeding manner, temperature, etc. should not cause deterioration of the catalyst. Patent Literature 1 focuses on the temperature of the sparse catalyst zone rather than the dense catalyst zone, and is intended to stably produce α,β-unsaturated nitrile such as acrylonitrile in a high yield over a long period of time by suppressing deterioration of a metal oxide catalyst, but the decrease in the yield of unsaturated nitrile is not only attributable to the deterioration of catalyst. According to the studies by the present inventors, it has been found that a part of unsaturated nitrile produced in a dense zone (dense catalyst zone) of the fluidized bed reactor further reacts with a catalyst in a sparse zone (sparse catalyst zone) and is decomposed.

The present invention has been made in the light of the above problem, and it is an object of the present invention to provide a process for producing unsaturated nitrile in which the unsaturated nitrile can be obtained in a high yield by suppressing decomposition of unsaturated nitrile produced in the fluidized bed reactor.

Solutions to Problems

That is, the present invention is as follows.

[1]

A process for producing unsaturated nitrile, using a fluidized bed reactor comprising an internal space comprising a catalyst capable of being fluidized therein; a feed opening to feed a starting material gas comprising hydrocarbon to the internal space; and a discharge port to discharge a reaction product gas from the internal space, the process comprising a reaction step of subjecting the hydrocarbon to a vapor phase catalytic ammoxidation reaction in the presence of the catalyst in the internal space to produce the corresponding unsaturated nitrile, wherein when in the internal space, a space where an existing amount of the catalyst per unit volume is 150 kg/m$^3$ or more is defined as a dense zone and a space where an existing amount of the catalyst per unit volume is less than 150 kg/m$^3$ is defined as a sparse zone in the reaction step, a gas residence time in the sparse zone is 5 to 50 sec.

[2]

The process for producing the unsaturated nitrile according to [1], wherein a superficial gas velocity in the sparse zone is less than 1 m/s in the reaction step.

[3]

The process for producing the unsaturated nitrile according to [1] or [2], wherein an oxygen concentration in the reaction product gas discharged from the discharge port is 0.1 vol % or more in the reaction step.

[4]

The process for producing the unsaturated nitrile according to any one of [1] to [3], wherein the oxygen concentration in the reaction product gas discharged from the discharge port is 0.1 vol % or more but 5.0 vol % or less in the reaction step.

[5]

The process for producing the unsaturated nitrile according to any one of [1] to [4], wherein when the oxygen concentration in the reaction product gas discharged from the discharge port is less than 2.0 vol % in the reaction step, the relation of (the gas residence time)≤7.5×(the oxygen concentration)+30 is satisfied, and when the oxygen concentration in the reaction product gas discharged from the discharge port is 2.0 vol % or more in the reaction step, the relation of (the gas residence time)≤−3×(the oxygen concentration)+50 is satisfied.

[6]

The process for producing the unsaturated nitrile according to any one of [1] to [5], wherein the hydrocarbon is propane and/or propylene.

Advantageous Effects of Invention

According to the present invention, a process for producing unsaturated nitrile in which the unsaturated nitrile can be obtained in a high yield by suppressing decomposition of the unsaturated nitrile produced in the fluidized bed reactor can be provided.

BRIEF DESCRIPTION OF DRAWINGS

FIG. 1 shows a schematic sectional view of a fluidized bed reactor that can be used in the process for producing unsaturated nitrile of the present embodiment.

DESCRIPTION OF EMBODIMENTS

An embodiment of the present invention (referred to as the "present embodiment" hereinafter) is described below in detail, but the present invention is not limited to this and can be variously modified without departing from the spirit of the present invention. In the drawings, the same elements are denoted by the same reference characters, and a repeated description thereof may be omitted. Unless otherwise noted, the positional relations such as up and down and left and right are based on the positional relations shown in the drawings. Further, the dimension ratios in the drawings are not limited to the ratios illustrated.

[Process for Producing Unsaturated Nitrile]

The process for producing unsaturated nitrile of the present embodiment is a process using a fluidized bed reactor comprising an internal space comprising a catalyst capable of being fluidized therein; a starting material feed opening to feed a starting material gas comprising hydrocarbon to the internal space; and a discharge port to discharge a reaction product gas from the internal space, the process comprising a reaction step of subjecting the hydrocarbon to a vapor phase catalytic ammoxidation reaction in the presence of the catalyst in the internal space to produce the corresponding unsaturated nitrile, wherein when in the internal space, a space where an existing amount of the catalyst per unit volume is 150 kg/m³ or more is defined as a dense zone and a space where an existing amount of the catalyst per unit volume is less than 150 kg/m³ is defined as a sparse zone in the reaction step, a gas residence time in the sparse zone is 5 to 50 sec.

In FIG. 1, a schematic sectional view of a fluidized bed reactor that can be used in the process for producing unsaturated nitrile of the present embodiment is shown.

The catalyst 2 is fluidized in the internal space 3 with a balance among the weight and the volume of the catalyst itself, the feed rates of the starting material gas A and the oxygen-containing gas B (flow rates in the direction of the arrow F), etc. In the zone above the dispersion tube 8, the existing amount (distribution) of the catalyst 2 in the internal space 3 per unit space decreases toward the upper part from the lower part of the internal space 3 (in the direction of the arrow F).

The average particle diameter of the catalyst 2 is preferably 35 to 75 µm. The bulk density of the catalyst 2 is preferably 0.85 to 1.2 g/cc.

The internal space 3 may have, in addition to the cyclone 7 to separate and recover the catalyst 2 from the reaction product gas, a cooling coil (not shown) to mainly remove heat of reaction of the dense zone of the internal space 3 and thereby control the reaction temperature and a member (not shown) to control the superficial gas velocity in the internal space 3, when needed. The superficial gas velocity in the internal space 3 varies with a cross-sectional area of the internal space 3 (area in a direction orthogonally intersecting with the direction of the arrow F). For example, when an internal space 3 whose cross-sectional areas are not uniform is supposed, the superficial gas velocity decreases at a place having a large cross-sectional area, and the superficial gas velocity increases at a place having a small cross-sectional area. From the viewpoint of control of the superficial gas velocity at each place of the internal space 3, the member to control the superficial gas velocity is installed in the internal space 3, and the gas-flowable cross-sectional area at a place where the member to control the superficial gas velocity is installed is narrowed by a portion occupied by the member to control the superficial gas velocity, so that the superficial gas velocity at this place increases as compared with that at a place where the member to control the superficial gas velocity is not installed. Instead of installing the member to control the superficial gas velocity, a fluidized bed reactor 1 whose diameters are not uniform so that the cross-sectional area of the internal space 3 may vary at the desired place may be used.

The reaction product gas accompanied by the catalyst 2 enters the cyclone 7 through an inlet 7a. The catalyst 2 having entered the cyclone 7 falls downward in the internal space 3 so as to be spiral in the conical section of the cyclone 7, while the reaction product gas is guided to the discharge port 6 by a tube extending upward from the upper part of the cyclone 7. Below the conical section of the cyclone 7, a tube further extends downward in the internal space 3, and through this tube, the catalyst 2 is guided downward in the internal space 3.

[Reaction Step]

The reaction step is a step of subjecting hydrocarbon to a vapor phase catalytic ammoxidation reaction in the presence of a catalyst to produce the corresponding unsaturated nitrile. The vapor phase catalytic ammoxidation reaction takes place mainly in the dense zone 3b.

The hydrocarbon is not specifically restricted, and examples thereof include alkanes, such as methane, ethane, propane, n-butane and isobutane; and alkenes, such as ethylene, propylene, n-butylene and isobutylene. Of these, propane, isobutane, propylene and isobutylene are preferable, and propane and/or propylene is more preferable, from the viewpoint of values of the resulting nitrile compound as an intermediate material for chemicals.

In the starting material gas A, starting materials other than hydrocarbon may be contained. Examples thereof include ammonia, oxygen and air. As previously described, oxygen, air or the like can also be fed as the oxygen-containing gas B separately from the starting material gas A.

The catalyst is not specifically restricted as long as it is a solid catalyst usually used for the vapor phase catalytic ammoxidation reaction, and for example, a metal oxide catalyst supported on silica or the like can be used.

The composition of the catalyst is not specifically restricted as long as it has an activity against the vapor phase catalytic ammoxidation reaction, but from the viewpoint that the action and effect of the present invention are exerted more effectively and more surely, an oxide catalyst containing at least molybdenum as an element (also referred to as an "oxide catalyst" simply hereinafter) is preferable. More specifically, a catalyst having a composition represented by the following formula (1) can be used.

$$MoV_aNb_bX_cT_dZ_eO_n \qquad (1)$$

wherein, a, b, c, d, e and n each represents an atomic ratio of each atom per Mo atom, and are in the ranges of 0.01≤a≤1, 0.01≤b≤1, 0.01≤c≤1, 0≤d<1, and 0≤e<1, and n is a value satisfying a balance of the valences.

Per Mo atom, the atomic ratio a of V is preferably 0.1 or more and 0.4 or less, and the atomic ratio b of Nb is preferably 0.01 or more and 0.2 or less. The atomic ratio c of the X component per Mo atom is preferably 0.01 or more and 0.6 or less, and is more preferably 0.1 or more and 0.4 or less.

The element represented by X is one or more elements selected from the group consisting of, for example, Sb, Te, Sr, Cr, Ta, Rh, Pd, Pt and Ag. Examples of compounds containing these elements include nitrates, carboxylates, carboxylic acid ammonium salts, peroxocarboxylates, peroxocarboxylic acid ammonium salts, halogenated ammonium salts, halides, acetylacetonates and alkoxides. Of these, aqueous starting materials represented by nitrates and carboxylates are preferably used.

As the elements represented by X, Te and Sb are preferable. In the industrial production process for unsaturated nitrile, properties of withstanding long-term use at not lower than 400° C. are generally required, and it is particularly preferable to use Sb as the element represented by X. On the other hand, in the industrial production process for an unsaturated acid, a reaction at not higher than 400° C. is also possible, and therefore, influence by escaping of Te in the long-term operation is small, so that also Te can be preferably used.

d that is an atomic ratio of an element represented by T per Mo atom is preferably 0 or more and 1 or less, more preferably 0.001 or more and 0.1 or less, and still more preferably 0.002 or more and 0.08 or less. The element represented by T is preferably one or more elements selected from the group consisting of Ti, Zr, Hf, W, Mn, Re, Fe, Co, Ni, Au, Zn, B, Al, Ga, In, Ge, Sn and Bi, and is more preferably Ti, W or Mn.

e that is an atomic ratio of an element represented by Z per Mo atom is preferably 0 or more and 1 or less, and more preferably 0.0001 or more and 0.5 or less. As the element represented by Z, one or more elements selected from the group consisting of rare earth elements and alkaline earth elements can be used, and preferable are Ba, Sc, Y, La, Ce, Pr and Yb, and particularly preferable is Ce. From the viewpoint of enhancement in yield of unsaturated nitrile in the ammoxidation reaction, it is preferable that the oxide catalyst contain an element represented by Z, and it is more preferable that the elements be homogeneously dispersed in a catalyst particle.

Examples of compounds containing Mo, which become starting materials for Mo in the catalyst, (referred to as "Mo-containing compounds" hereinafter, the same shall apply to other elements) include ammonium molybdate oxide, ammonium heptamolybdate, phosphomolybdic acid and silicomolybdic acid, and of these, ammonium heptamolybdate $[(NH_4)_6Mo_7O_{24} \cdot 4H_2O]$ can be preferably used.

Examples of V-containing compounds that become starting materials for V in the catalyst include vanadium pentoxide, ammonium metavanadate and vanadyl sulfate, and of these, ammonium metavanadate $[NH_4VO_3]$ can be preferably used.

Examples of Nb-containing compounds that become starting materials for Nb in the catalyst include niobic acid, inorganic acid salts of niobium and organic acid salts of niobium, and of these, niobic acid can be preferably used.

When Te is used as an element represented by X, telluric acid $[H_6TeO_6]$ can be preferably used as a starting material for Te in the catalyst, and when Sb is used, antimony oxide, particularly antimony trioxide $[Sb_2O_3]$, can be preferably used as a starting material for Sb in the catalyst.

When the oxide catalyst is supported on silica, silica sol, powder silica or the like can be added as a starting material for silica. The powder silica is preferably one produced by a pyrogenic method, and by dispersing the powder silica in water in advance and using the resulting dispersion, addition to a slurry and mixing become easy. The dispersing method is not specifically restricted, and dispersing can be carried out using general homogenizer, homomixer, ultrasonic vibrator, etc. singly or in combination.

The oxide catalyst can be obtained by preparing an aqueous solution or an aqueous dispersion of these starting materials and subjecting the solution or the dispersion to drying and calcining in accordance with conventional methods.

In the present embodiment, the internal space 3 where a vapor phase catalytic ammoxidation reaction is being carried out is defined by dividing it into a dense zone 3b in which an existing amount of the catalyst per unit volume is 150 kg/m$^3$ or more and a sparse zone 3a which is located between the dense zone and the discharge port and in which an existing amount of the catalyst per unit volume is less than 150 kg/m$^3$.

At this time, the gas residence time in the sparse zone is 5 to 50 sec, preferably 6 to 45 sec, and more preferably 7 to 40 sec. Since the gas residence time in the sparse zone is 5 sec or more, abrasion of the catalyst due to collision of the catalyst with the cyclone 7 or outflow of the catalyst from the discharge port can be suppressed, and in the case of continuous operation, a decrease in the yield of unsaturated nitrile can be suppressed. Since the gas residence time in the sparse zone is 50 sec or less, the contact time of the catalyst with the unsaturated nitrile in the sparse zone is reduced, and the unsaturated nitrile produced in the dense zone 3b can be inhibited from being decomposed in the sparse zone 3a, so that the yield of the resulting unsaturated nitrile is further enhanced.

As a technique to control the gas residence time in the sparse zone to the above range, a technique of changing the flow rate of the starting material gas or the oxygen-containing gas, a technique of changing the temperature of the fluidized bed reactor 1, a technique of changing the pressure in the fluidized bed reactor 1, a technique of changing the volume of the fluidized bed reactor 1 by means of a member or the like of the reactor, or a technique of a combination of them can be used.

The gas residence time in the sparse zone can be calculated from the following formula.

Gas residence time in sparse zone(sec)=(space volume of sparse zone(m$^3$)×3600)/gas flow rate in sparse zone(m$^3$/hr)

The "gas flow rate in sparse zone" is determined by the feed rate of gases fed to the internal space, such as starting material gas and oxygen-containing gas, taking into consideration expansion and contraction due to the temperature and the pressure in the sparse zone, and is calculated from the following formula.

Gas flow rate in sparse zone(m$^3$/hr)=(feed rate of gas fed to internal space(Nm$^3$/hr))×(sparse zone temperature(° C.)+273.15)/273.15×1.033/ (1.033+pressure in reactor(K/G))

As a technique to control the existing amount of the catalyst in the sparse zone per unit volume and the existing amount of the catalyst in the dense zone per unit volume to the above ranges, a technique of controlling the superficial gas velocity at each place in the reactor, a technique of controlling the bulk specific gravity of the catalyst, or a technique of a combination of them can be used.

The "existing amount of the catalyst per unit volume" in the present embodiment can be calculated from the following formula using a fluidized bed differential pressure. In the internal space of the fluidized bed reactor, the pressure at each height is measured by a manometer installed at each of a plurality of measurement points different in height, and the existing amount of the catalyst is calculated to specify the ranges of the sparse zone and the dense zone, whereby the space volume of the sparse zone can be calculated. The existing amount (kg/m$^3$) of the catalyst per unit volume present in an internal space surrounded by cross sections of the fluidized bed reactor, which has been cut in the horizontal direction to the ground surface at a distance h1 (m) measured from the ground surface in the vertical direction to the ground surface and a distance h2 (m) measured from the ground surface in the vertical direction to the ground surface (h2>h1), and the fluidized bed reactor is represented by the following formula.

Existing amount of catalyst from $h1$ to $h2$ per unit volume (kg/m$^3$)=(differential pressure between $h2$–$h1$ (Pa))/(9.8 (m/s$^2$)×distance between $h2$–$h1$ ($m$))

When the highest value of measured values that are each less than 150 kg/m$^3$ among the existing amounts of the catalyst per unit volume calculated from the above formula is represented by D3 (kg/m$^3$), the distance between the ground surface and this measurement point, which is measured in the vertical direction to the ground surface, is represented by h3 (m), the lowest value of measured values that are each 150 kg/m$^3$ or more among the above existing amounts is represented by D4 (kg/m$^3$), and the distance between the ground surface and this measurement point, which is measured in the vertical direction to the ground surface, is represented by h4 (m), a distance h5 (m) from the ground surface measured in the vertical direction to the ground surface is calculated from the following formula, and a cross section of the fluidized bed reactor cut at this distance in the horizontal direction to the ground surface is a boundary plane between the sparse zone 3a and the dense zone 3b.

$h5(m)=((150-D3)\times h4+(D4-150)\times h3)/(D4-D3)$

When the distance between the ground surface and the upper end of the reactor, which is measured in the vertical direction to the ground surface, is represented by h6 (m), the sparse zone space volume (m$^3$) is calculated from the following formula.

Sparse zone space volume $(m^3)=(h6(m)-h5(m))\times$ (effective cross-sectional area of sparse zone $(m^2)$)

The sparse zone temperature (° C.) is an addition mean value of the maximum temperature and the minimum temperature among the temperatures measured inside the reactor.

In the reaction step, the superficial gas velocity in the sparse zone 3a is preferably less than 1 m/sec, more preferably less than 0.95 m/sec, and still more preferably less than 0.9 m/sec. By controlling the superficial gas velocity to less than 1 m/s, the existing amount of the catalyst in the sparse zone can be reduced, and the unsaturated nitrile produced in the dense zone 3b can be inhibited from being decomposed in the sparse zone 3a, so that the yield of the resulting unsaturated nitrile tends to be further enhanced. The lower limit of the superficial gas velocity in the sparse zone 3a is not specifically restricted, but the superficial gas velocity is preferably 0.1 m/sec or more, more preferably 0.3 m/sec or more, and still more preferably 0.4 m/sec or more. The superficial gas velocity in the present embodiment can be calculated from the following formula. The "effective cross-sectional area of sparse zone" refers to a mean value of areas of cross sections through which the gas passes in the sparse zone (in the case where a member to decrease the superficial gas velocity is present in the sparse zone, this term refers to a mean value of cross-sectional areas except the cross-sectional area of the member). This mean value is an addition mean value of the largest cross-sectional area and the smallest cross-sectional area in the sparse zone. The "gas flow rate in sparse zone" is determined by the total amount of gases fed to the internal space, such as starting material gas and oxygen-containing gas.

Superficial gas velocity in sparse zone(m/sec)=gas flow rate in sparse zone(m$^3$/hr)/effective cross-sectional area of sparse zone(m$^2$)/3600

If the oxygen concentration in the reaction product gas C discharged from the discharge port 6 is 0.1 vol % or less, the catalyst is excessively reduced, and a phenomenon of a decrease in activity takes place, so that the yield of the desired product cannot be maintained. In the reaction step, therefore, the oxygen concentration in the reaction product gas C discharged from the discharge port 6 is preferably 0.1 vol % or more, more preferably 0.5 vol % or more, and still more preferably 1.0 vol % or more.

When the oxygen concentration in the reaction product gas C is less than 2.0 vol % and when the gas residence time in the sparse zone is long, reduction of the catalyst is further accelerated, and therefore, the oxygen concentration (vol %) in the reaction product gas C and the gas residence time (sec) in the sparse zone preferably satisfy the following relational formula.

Gas residence time in sparse zone(sec)≤7.5×(oxygen concentration in reaction product gas discharged from discharge port(vol %))+30

On the other hand, when the oxygen concentration in the reaction product gas C is 0.1% or more, the catalyst is oxidized, whereby there occurs a phenomenon that the activity increases, and in the sparse zone 3a, a reaction to decompose the unsaturated nitrile produced in the dense zone 3b is accelerated, the temperature of the gas staying in the sparse zone 3a rises, and in the sparse zone 3a, a reaction to decompose the unsaturated nitrile produced in the dense zone 3b is further accelerated. With regard to this phenomenon, by controlling the residence time of the gas in the sparse zone 3a to 5 to 50 seconds, the unsaturated nitrile produced in the dense zone 3b can be inhibited from being decomposed in the sparse zone 3a, and the yield of the resulting unsaturated nitrile tends to be further enhanced. Accordingly, the oxygen concentration in the reaction product gas C discharged from the discharge port 6 is preferably 5.0 vol % or less, more preferably 3.5 vol % or less, and still more preferably 2.5 vol % or less. In the case where the oxygen concentration in the reaction product gas C is 2.0 vol % or more, the reaction to decompose the unsaturated nitrile produced in the dense zone 3b tends to be accelerated in the sparse zone 3a as the oxygen concentration increases, and therefore, the residence time in the sparse zone, the oxygen concentration (vol %) in the reaction product gas C and the gas residence time (sec) in the sparse zone preferably satisfy the following relational formula. The oxygen concentration in the reaction product gas C can be controlled by the feed rate of the oxygen-containing gas B or the reaction conditions.

Gas residence time in sparse zone(sec)≤-3.0×(oxygen concentration in reaction product gas discharged from discharge port(vol %))+50

EXAMPLES

The present invention will be more specifically described below with reference to examples and comparative examples. The present invention is in no way limited to the following examples.

Example 1

A fluidized bed reactor 1 similar to that shown in FIG. 1 was prepared. The fluidized bed reactor 1 was in the form of a vertical cylinder having an inner diameter of 0.6 m and a length of 17.5 m, had a dispersion plate 5 at the position of 1 m from a lower end of an internal space 3 and a starting material feed opening 4 above the dispersion plate in such a way that they faced each other, and had a lower end of an opening of a cyclone 7 at the position of 15.5 m from an upper end of the internal space 3.

The fluidized bed reactor was filled with 550 kg of a catalyst $(Mo_1V_{0.207}Sb_{0.219}Nb_{0.102}W_{0.030}Ce_{0.005}O_n/51.0$ wt $\%\text{-SiO}_2)$ described in Example 1 of Japanese Patent No. 5694379, and propane and ammonia that were reaction starting materials were fed from the starting material feed opening 4 and air was fed from the dispersion plate 5 through a feed opening 9 in such a way that the propane:ammonia:oxygen molar ratio became 1:1.1:2.8 at a reaction temperature of 445° C. and a reaction pressure of normal pressure. The yield of acrylonitrile after 3 hours (immediately after starting) and the yield of acrylonitrile after one week, from the initiation of the vapor phase catalytic ammoxidation reaction, are set forth in Table 1.

Example 2

A vapor phase catalytic ammoxidation reaction was carried out in the same manner as in Example 1, except that the catalytic amount was changed to 700 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 3

A vapor phase catalytic ammoxidation reaction was carried out in the same manner as in Example 1, except that the catalytic amount was changed to 380 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 4

A vapor phase catalytic ammoxidation reaction was carried out in the same manner as in Example 1, except that a member to control the volume of the internal space was arranged to change the space volume of the sparse zone as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 5

A vapor phase catalytic ammoxidation reaction was carried out in the same manner as in Example 1, except that a member to control the volume of the internal space was removed to change the space volume of the sparse zone as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 6

A vapor phase catalytic ammoxidation reaction was carried out in the same manner as in Example 1, except that the catalytic amount was changed to 380 kg, the gas flow rate was changed as shown in Table 1, and a member to control the volume of the internal space was arranged to change the space volume of the sparse zone as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 7

A vapor phase catalytic ammoxidation reaction was carried out in the same manner as in Example 1, except that the molar ratio of the starting material gas was changed to propane:ammonia:oxygen=1:1.1:2.3. The yield of acrylonitrile after 3 hours (immediately after starting) and the yield of acrylonitrile after one week, from the initiation of the vapor phase catalytic ammoxidation reaction, are set forth in Table 1.

Example 8

A vapor phase catalytic ammoxidation reaction was carried out in the same manner as in Example 1, except that the molar ratio of the starting material gas was changed to propane:ammonia:oxygen=1:1.1:3.4. The yield of acrylonitrile after 3 hours (immediately after starting) and the yield of acrylonitrile after one week, from the initiation of the vapor phase catalytic ammoxidation reaction, are set forth in Table 1.

Example 9

A vapor phase catalytic ammoxidation reaction was carried out in the same manner as in Example 1, except that the temperature of the sparse zone was set at 460° C. The yield of acrylonitrile after 3 hours (immediately after starting) and the yield of acrylonitrile after one week, from the initiation of the vapor phase catalytic ammoxidation reaction, are set forth in Table 1.

Example 10

A vapor phase catalytic ammoxidation reaction was carried out in the same manner as in Example 1, except that the temperature of the sparse zone was set at 440° C. The yield of acrylonitrile after 3 hours (immediately after starting) and the yield of acrylonitrile after one week, from the initiation of the vapor phase catalytic ammoxidation reaction, are set forth in Table 1.

Example 11

A vapor phase catalytic ammoxidation reaction was carried out in the same manner as in Example 1, except that a fluidized bed reactor 1 which was similar to that shown in FIG. 1, was in the form of a vertical cylinder having an inner diameter of 10 m and a length of 30 m, had a dispersion plate 5 at the position of 3 m from a lower end of an internal space 3 and a starting material feed opening 4 above the dispersion plate in such a way that they faced each other, and had a lower end of an opening of a cyclone 7 at the position of 21.0 m from an upper end of the internal space 3 was used, the catalytic amount was changed to 155000 kg, and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 12

A vapor phase catalytic ammoxidation reaction was carried out in the same manner as in Example 1, except that the catalyst for filling was changed to a catalyst ($Mo_1V_{0.207}Sb_{0.219}Nb_{0.102}W_{0.030}Ce_{0.005}O_n$/68.0 wt %-$SiO_2$) described in Example 3 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 1.

Example 13

A vapor phase catalytic ammoxidation reaction was carried out in the same manner as in Example 1, except that the catalyst for filling was changed to a catalyst ($Mo_1V_{0.240}Sb_{0.250}Nb_{0.120}W_{0.030}Ce_{0.005}O_n$/51.0 wt %-$SiO_2$) described in Example 4 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 2.

Example 14

A vapor phase catalytic ammoxidation reaction was carried out in the same manner as in Example 6, except that the feed rate of the gas fed to the internal space was changed as shown in Table 2. The yield of acrylonitrile after 3 hours (immediately after starting) and the yield of acrylonitrile after one week, from the initiation of the vapor phase catalytic ammoxidation reaction, are set forth in Table 2.

Example 15

A vapor phase catalytic ammoxidation reaction was carried out in the same manner as in Example 6, except that the feed rate of the starting material gas fed to the internal space was changed as shown in Table 2, and the molar ratio of the starting material gas was changed to propane:ammonia:oxygen=1:1.1:3.0. The yield of acrylonitrile after 3 hours (immediately after starting) and the yield of acrylonitrile after one week, from the initiation of the vapor phase catalytic ammoxidation reaction, are set forth in Table 2.

Example 16

A vapor phase catalytic ammoxidation reaction was carried out in the same manner as in Example 6, except that the molar ratio of the starting material gas was changed to propane:ammonia:oxygen=1:1.1:3.4. The yield of acrylonitrile after 3 hours (immediately after starting) and the yield of acrylonitrile after one week, from the initiation of the vapor phase catalytic ammoxidation reaction, are set forth in Table 2.

Example 17

A vapor phase catalytic ammoxidation reaction was carried out in the same manner as in Example 1, except that the molar ratio of the starting material gas was changed to propane:ammonia:oxygen=1:1.1:3.0. The yield of acrylonitrile after 3 hours (immediately after starting) and the yield of acrylonitrile after one week, from the initiation of the vapor phase catalytic ammoxidation reaction, are set forth in Table 2.

Example 18

A vapor phase catalytic ammoxidation reaction was carried out in the same manner as in Example 15, except that the feed rate of the starting material gas fed to the internal space was changed as shown in Table 2. The yield of acrylonitrile after 3 hours (immediately after starting) and the yield of acrylonitrile after one week, from the initiation of the vapor phase catalytic ammoxidation reaction, are set forth in Table 2.

Example 19

A vapor phase catalytic ammoxidation reaction was carried out in the same manner as in Example 8, except that the feed rate of the starting material gas fed to the internal space was changed as shown, in Table 2. The yield of acrylonitrile after 3 hours (immediately after starting) and the yield of acrylonitrile after one week, from the initiation of the vapor phase catalytic ammoxidation reaction, are set forth in Table 2.

Example 20

A vapor phase catalytic ammoxidation reaction was carried out in the same manner as in Example 1, except that the molar ratio of the starting material gas was changed to propane:ammonia:oxygen=1:1.1:3.6. The yield of acrylonitrile after 3 hours (immediately after starting) and the yield of acrylonitrile after one week, from the initiation of the vapor phase catalytic ammoxidation reaction, are set forth in Table 2.

Example 21

In a fluidized bed reactor, a catalyst in which 60 mass % of a composite oxide having a metal component composition represented by $Mo_{12.00}Bi_{0.39}Fe_{1.60}Ni_{6.97}Mg_{0.77}Ce_{0.63}Rb_{0.17}$ was supported on 40 mass % of silica was produced by the following procedure.

(Preparation Example) Starting Material Mixed Liquid

First, to 1333 g of an aqueous silica sol containing 30 mass % of $SiO_2$, 485.9 g of ammonium paramolybdate [$(NH_4)_6Mo_7O_{24} \cdot 4H_2O$] having been dissolved in 873.5 g of water was added with stirring, thereby obtaining a first solution containing molybdenum and silica. Next, in 396.7 g of nitric acid of 16.6 mass %, 43.1 g of bismuth nitrate [$Bi(NO_3)_3 \cdot 5H_2O$], 148.0 g of iron nitrate [$Fe(NO_3)_3 \cdot 9H_2O$], 464.7 g of nickel nitrate [$Ni(NO_3)_2 \cdot 6H_2O$], 45.5 g of magnesium nitrate [Mg(NO$_3$)$_2$.6H$_2$O], 62.6 g of cerium nitrate [Ce(NO$_3$)$_3$.6H$_2$O] and 5.89 g of rubidium nitrate [RbNO$_3$] were dissolved, thereby obtaining a second solution. The second solution was mixed with the first solution, thereby obtaining a starting material mixed liquid in the form of a slurry.

(Preparation Example) Catalyst

Using a first drying device, the resulting starting material mixed liquid of 40° C. was dried in the same manner as in Example 1, except that the temperature of hot air was set at 230° C. immediately before the drying chamber and was set at 110° C. immediately after discharging. The resulting dry powder was maintained at 200° C. for 5 minutes, then heated from 200° C. up to 450° C. at 2.5° C./min and maintained at 450° C. for 20 minutes to denitrate the powder. The resulting denitrated powder was calcined at 580° C. for 2 hours, thereby obtaining a catalyst.

The fluidized bed reactor was filled with 700 kg of the resulting catalyst, and propylene and ammonia that were reaction starting materials were fed from the starting material feed opening 4 and air was fed from the dispersion plate 5 through a feed opening 9 in such a way that the propylene:ammonia:oxygen molar ratio became 1:1.1:1.8 at a reaction temperature of 450° C. and a reaction pressure of 0.50 K/G. The yield of acrylonitrile after 3 hours (immediately after starting) and the yield of acrylonitrile after one week, from the initiation of the vapor phase catalytic ammoxidation reaction, are set forth in Table 2.

Example 22

A vapor phase catalytic ammoxidation reaction was carried out in the same manner as in Example 21, except that a member to control the volume of the internal space was removed to change the space volume of the sparse zone as shown in Table 2. The yield of acrylonitrile after 3 hours (immediately after starting) and the yield of acrylonitrile after one week, from the initiation of the vapor phase catalytic ammoxidation reaction, are set forth in Table 2.

Example 23

A vapor phase catalytic ammoxidation reaction was carried out in the same manner as in Example 21, except that the feed rate of the starting material gas fed to the internal space was changed as shown in Table 2, and the molar ratio of the starting material gas was changed to propylene:ammonia:oxygen=1:1.1:2.4. The yield of acrylonitrile after 3 hours (immediately after starting) and the yield of acrylonitrile after one week, from the initiation of the vapor phase catalytic ammoxidation reaction, are set forth in Table 2.

Example 24

A vapor phase catalytic ammoxidation reaction was carried out in the same manner as in Example 22, except that the feed rate of the starting material gas fed to the internal space was changed as shown in Table 2. The yield of acrylonitrile after 3 hours (immediately after starting) and the yield of acrylonitrile after one week, from the initiation of the vapor phase catalytic ammoxidation reaction, are set forth in Table 2.

Comparative Example 1

A vapor phase catalytic ammoxidation reaction was carried out in the same manner as in Example 1, except that a member to control the volume of the internal space was arranged to change the space volume of the sparse zone as shown in Table 3. The yield of acrylonitrile after 3 hours (immediately after starting) and the yield of acrylonitrile after one week, from the initiation of the vapor phase catalytic ammoxidation reaction, are set forth in Table 3.

Comparative Example 2

A vapor phase catalytic ammoxidation reaction was carried out in the same manner as in Example 5, except that the catalytic amount was changed to 380 kg, the gas flow rate was changed as shown in Table 3, and the molar ratio of the starting material gas was changed to propane:ammonia:oxygen=1:1.1:3.0. The yield of acrylonitrile after 3 hours (immediately after starting) and the yield of acrylonitrile after one week, from the initiation of the vapor phase catalytic ammoxidation reaction, are set forth in Table 3.

Comparative Example 3

A vapor phase catalytic ammoxidation reaction was carried out in the same manner as in Comparative Example 1, except that the molar ratio of the starting material gas was changed to propane:ammonia:oxygen=1:1.1:3.0. The yield of acrylonitrile after 3 hours (immediately after starting) and the yield of acrylonitrile after one week, from the initiation of the vapor phase catalytic ammoxidation reaction, are set forth in Table 3.

Comparative Example 4

A vapor phase catalytic ammoxidation reaction was carried out in the same manner as in Example 11, except that a member to control the volume of the internal space was arranged to change the space volume of the sparse zone as shown in Table 3. The yield of acrylonitrile after 3 hours (immediately after starting) and the yield of acrylonitrile after one week, from the initiation of the vapor phase catalytic ammoxidation reaction, are set forth in Table 3.

Comparative Example 5

A vapor phase catalytic ammoxidation reaction was carried out in the same manner as in Example 11, except that the catalytic amount was changed to 130000 kg and the gas flow rate was changed as shown in Table 3. The yield of acrylonitrile after 3 hours (immediately after starting) and the yield of acrylonitrile after one week, from the initiation of the vapor phase catalytic ammoxidation reaction, are set forth in Table 3.

Comparative Example 6

A vapor phase catalytic ammoxidation reaction was carried out in the same manner as in Comparative Example 1, except that the catalyst for filling was changed to a catalyst (Mo$_1$V$_{0.207}$Sb$_{0.219}$Nb$_{0.102}$W$_{0.030}$Ce$_{0.005}$O$_n$/68.0 wt %-SiO$_2$) described in Example 3 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 3.

Comparative Example 7

A vapor phase catalytic ammoxidation reaction was carried out in the same manner as in Comparative Example 2, except that the catalyst for filling was changed to a catalyst $(Mo_1V_{0.207}Sb_{0.219}Nb_{0.102}W_{0.030}Ce_{0.005}O_n/68.0$ wt %-$SiO_2)$ described in Example 3 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 3.

Comparative Example 8

A vapor phase catalytic ammoxidation reaction was carried out in the same manner as in Comparative Example 1, except that the catalyst for filling was changed to a catalyst $(Mo_1V_{0.240}Sb_{0.250}Nb_{0.120}W_{0.030}Ce_{0.005}O_n/51.0$ wt %-$SiO_2)$ described in Example 4 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 3.

Comparative Example 9

A vapor phase catalytic ammoxidation reaction was carried out in the same manner as in Comparative Example 2, except that the catalyst for filling was changed to a catalyst $(Mo_1V_{0.240}Sb_{0.250}Nb_{0.120}W_{0.030}Ce_{0.005}O_n/51.0$ wt %-$SiO_2)$ described in Example 4 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 3.

Comparative Example 10

A vapor phase catalytic ammoxidation reaction was carried out in the same manner as in Comparative Example 9, except that the molar ratio of the starting material gas was changed to propane:ammonia:oxygen=1:1.1:2.2. The yield of acrylonitrile after 3 hours (immediately after starting) and the yield of acrylonitrile after one week, from the initiation of the vapor phase catalytic ammoxidation reaction, are set forth in Table 3.

Comparative Example 11

A vapor phase catalytic ammoxidation reaction was carried out in the same manner as in Comparative Example 9, except that the molar ratio of the starting material gas was changed to propane:ammonia:oxygen=1:1.1:3.0. The yield of acrylonitrile after 3 hours (immediately after starting) and the yield of acrylonitrile after one week, from the initiation of the vapor phase catalytic ammoxidation reaction, are set forth in Table 3.

Comparative Example 12

A vapor phase catalytic ammoxidation reaction was carried out in the same manner as in Comparative Example 9, except that the molar ratio of the starting material gas was changed to propane:ammonia:oxygen=1:1.1:3.4. The yield of acrylonitrile after 3 hours (immediately after starting) and the yield of acrylonitrile after one week, from the initiation of the vapor phase catalytic ammoxidation reaction, are set forth in Table 3.

Comparative Example 13

A vapor phase catalytic ammoxidation reaction was carried out in the same manner as in Comparative Example 8, except that the molar ratio of the starting material gas was changed to propane:ammonia:oxygen=1:1.1:3.0. The yield of acrylonitrile after 3 hours (immediately after starting) and the yield of acrylonitrile after one week, from the initiation of the vapor phase catalytic ammoxidation reaction, are set forth in Table 3.

Comparative Example 14

A vapor phase catalytic ammoxidation reaction was carried out in the same manner as in Comparative Example 8, except that the molar ratio of the starting material gas was changed to propane:ammonia:oxygen=1:1.1:3.4. The yield of acrylonitrile after 3 hours (immediately after starting) and the yield of acrylonitrile after one week, from the initiation of the vapor phase catalytic ammoxidation reaction, are set forth in Table 3.

Comparative Example 15

A vapor phase catalytic ammoxidation reaction was carried out in the same manner as in Example 21, except that the temperature of the sparse zone was set at 440° C., and a member to control the volume of the internal space was arranged to change the space volume of the sparse zone as shown in Table 3. The yield of acrylonitrile after 3 hours (immediately after starting) and the yield of acrylonitrile after one week, from the initiation of the vapor phase catalytic ammoxidation reaction, are set forth in Table 3.

TABLE 1

| Example Comparative Example | Starting material gas | Feed rate of gas fed to internal space (Nm3/hr) | Gas flow rate in sparse zone (m3/hr) | Pressure in reactor (K/G) | Sparse zone temperature (° C.) | Sparse zone space volume (m3) | Sparse zone gas residence time (sec) | Superficial gas velocity (m/sec) | Reactor exit oxygen concentration (vol %) | AN yield immediately after starting (%) | AN yield after one week (%) |
|---|---|---|---|---|---|---|---|---|---|---|---|
| Ex. 1 | Propane | 420 | 703 | 0.60 | 450 | 2.7 | 13.8 | 0.74 | 2.0 | 55.1 | 55.2 |
| Ex. 2 | Propane | 530 | 888 | 0.60 | 450 | 2.7 | 11.0 | 0.94 | 2.0 | 55.1 | 55.1 |
| Ex. 3 | Propane | 280 | 469 | 0.60 | 450 | 2.7 | 20.7 | 0.49 | 2.0 | 54.9 | 54.8 |
| Ex. 4 | Propane | 420 | 703 | 0.60 | 450 | 1.8 | 9.2 | 1.11 | 2.0 | 55.2 | 55.2 |
| Ex. 5 | Propane | 420 | 703 | 0.60 | 450 | 5 | 25.6 | 0.40 | 2.0 | 54.8 | 54.9 |
| Ex. 6 | Propane | 280 | 469 | 0.60 | 450 | 5 | 38.4 | 0.27 | 2.0 | 54.7 | 54.7 |
| Ex. 7 | Propane | 420 | 703 | 0.60 | 450 | 2.7 | 13.8 | 0.74 | 0.5 | 55.4 | 54.6 |
| Ex. 8 | Propane | 420 | 703 | 0.60 | 450 | 2.7 | 13.8 | 0.74 | 5.0 | 54.6 | 54.3 |
| Ex. 9 | Propane | 420 | 713 | 0.60 | 460 | 2.7 | 13.6 | 0.75 | 2.0 | 54.1 | 54.2 |
| Ex. 10 | Propane | 420 | 694 | 0.60 | 440 | 2.7 | 14.0 | 0.73 | 2.0 | 55.4 | 55.5 |
| Ex. 11 | Propane | 120000 | 200966 | 0.60 | 450 | 1166 | 20.9 | 0.81 | 2.0 | 54.5 | 54.6 |
| Ex. 12 | Propane | 420 | 703 | 0.60 | 450 | 2.7 | 13.8 | 0.74 | 2.0 | 54.7 | 54.8 |

TABLE 2

| Example Comparative Example | Starting material gas | Feed rate of gas fed to internal space (Nm3/hr) | Gas flow rate in sparse zone (m3/hr) | Pressure in reactor (K/G) | Sparse zone temperature (° C.) | Sparse zone space volume (m3) | Sparse zone gas residence time (sec) | Superficial gas velocity (m/sec) | Reactor exit oxygen concentration (vol %) | AN yield immediately after starting (%) | AN yield after one week (%) |
|---|---|---|---|---|---|---|---|---|---|---|---|
| Ex. 13 | Propane | 420 | 703 | 0.60 | 450 | 2.7 | 13.8 | 0.74 | 2.0 | 54.6 | 54.7 |
| Ex. 14 | Propane | 230 | 385 | 0.60 | 450 | 5 | 46.7 | 0.22 | 2.0 | 54.0 | 54.1 |
| Ex. 15 | Propane | 250 | 419 | 0.60 | 450 | 5 | 43.0 | 0.24 | 3.0 | 53.8 | 53.9 |
| Ex. 16 | Propane | 280 | 469 | 0.60 | 450 | 5 | 38.4 | 0.27 | 5.0 | 53.5 | 53.6 |
| Ex. 17 | Propane | 420 | 703 | 0.60 | 450 | 2.7 | 13.8 | 0.74 | 3.0 | 54.5 | 54.6 |
| Ex. 18 | Propane | 350 | 586 | 0.60 | 450 | 5 | 30.7 | 0.33 | 3.0 | 54.7 | 54.5 |
| Ex. 19 | Propane | 280 | 469 | 0.60 | 450 | 2.7 | 20.7 | 0.49 | 5.0 | 54.5 | 54.4 |
| Ex. 20 | Propane | 420 | 703 | 0.60 | 450 | 2.7 | 13.8 | 0.74 | 5.5 | 53.5 | 53.5 |
| Ex. 21 | Propylene | 420 | 750 | 0.50 | 450 | 2.7 | 13.0 | 0.79 | 0.3 | 82.0 | 82.1 |
| Ex. 22 | Propylene | 420 | 750 | 0.50 | 450 | 5 | 24.0 | 0.43 | 0.3 | 81.5 | 81.4 |
| Ex. 23 | Propylene | 280 | 500 | 0.50 | 450 | 5 | 36.0 | 0.28 | 3.0 | 81.8 | 81.7 |
| Ex. 24 | Propylene | 220 | 392 | 0.50 | 450 | 5 | 45.9 | 0.22 | 0.3 | 81.0 | 80.8 |

TABLE 3

| Example Comparative Example | Starting material gas | Feed rate of gas fed to internal space (Nm3/hr) | Gas flow rate in sparse zone (m3/hr) | Pressure in reactor (K/G) | Sparse zone temperature (° C.) | Sparse zone space volume (m3) | Sparse zone gas residence time (sec) | Superficial gas velocity (m/sec) | Reactor exit oxygen concentration (vol %) | AN yield immediately after starting (%) | AN yield after one week (%) | |
|---|---|---|---|---|---|---|---|---|---|---|---|---|
| Comp. Ex. 1 | Propane | 420 | 703 | 0.60 | 450 | 0.8 | 4.1 | 2.50 | 2.0 | 55.1 | — | *1 |
| Comp. Ex. 2 | Propane | 200 | 335 | 0.60 | 450 | 5 | 53.7 | 0.19 | 2.0 | 50.2 | 50.3 | |
| Comp. Ex. 3 | Propane | 420 | 703 | 0.60 | 450 | 0.8 | 4.1 | 2.50 | 0.5 | 55.4 | — | *1 |
| Comp. Ex. 4 | Propane | 120000 | 200966 | 0.60 | 450 | 250 | 4.5 | 3.76 | 2.0 | 54.2 | — | *1 |
| Comp. Ex. 5 | Propane | 48000 | 80386 | 0.60 | 450 | 1166 | 52.2 | 0.32 | 2.0 | 49.7 | 49.5 | |
| Comp. Ex. 6 | Propane | 420 | 703 | 0.60 | 450 | 0.8 | 4.1 | 2.50 | 2.0 | 54.7 | — | *1 |
| Comp. Ex. 7 | Propane | 200 | 335 | 0.60 | 450 | 5 | 53.7 | 0.19 | 2.0 | 49.8 | 49.9 | |
| Comp. Ex. 8 | Propane | 420 | 703 | 0.60 | 450 | 0.8 | 4.1 | 2.50 | 2.0 | 54.6 | — | *1 |
| Comp. Ex. 9 | Propane | 200 | 335 | 0.60 | 450 | 5 | 53.7 | 0.19 | 2.0 | 49.7 | 49.8 | |
| Comp. Ex. 10 | Propane | 200 | 335 | 0.60 | 450 | 5 | 53.7 | 0.19 | 0.3 | 48.5 | 48.2 | |
| Comp. Ex. 11 | Propane | 200 | 335 | 0.60 | 450 | 5 | 53.7 | 0.19 | 3.0 | 49.8 | 49.9 | |
| Comp. Ex. 12 | Propane | 200 | 335 | 0.60 | 450 | 5 | 53.7 | 0.19 | 5.0 | 49.8 | 49.9 | |
| Comp. Ex. 13 | Propane | 420 | 703 | 0.60 | 450 | 0.8 | 4.1 | 2.50 | 3.0 | 54.5 | — | *1 |
| Comp. Ex. 14 | Propane | 420 | 703 | 0.60 | 450 | 0.8 | 4.1 | 2.50 | 5.0 | 54.4 | — | *1 |
| Comp. Ex. 15 | Propylene | 420 | 739 | 0.50 | 440 | 0.8 | 3.9 | 2.63 | 0.3 | 82.0 | — | *1 |

*1: Continuing of reaction is impossible because of scattering of catalyst.

INDUSTRIAL APPLICABILITY

The present invention has industrial applicability as a process for producing unsaturated nitrile.

REFERENCE SIGNS LIST

1: fluidized bed reactor, 2: catalyst, 3: internal space, 3a: upper space, 3b: lower space, 4: starting material feed opening, 5: dispersion plate, 6: discharge port, 7: cyclone, 7a: inlet, 8: dispersion tube, 9: feed opening, A: starting material gas, B: oxygen-containing gas, C: reaction product gas

The invention claimed is:

1. A process for producing unsaturated nitrile, using a fluidized bed reactor having an internal space comprising a catalyst capable of being fluidized therein; a feed opening to feed a starting material gas comprising hydrocarbon to the internal space; and a discharge port to discharge a reaction product gas from the internal space, the process comprising a reaction step of subjecting the hydrocarbon to a vapor phase catalytic ammoxidation reaction in the presence of the catalyst in the internal space to produce the corresponding unsaturated nitrile, wherein when in the internal space, a space where an existing amount of the catalyst per unit volume is 150 kg/m$^3$ or more is defined as a dense zone and a space where an existing amount of the catalyst per unit volume is less than 150 kg/m$^3$ is defined as a sparse zone in the reaction step, a gas residence time in the sparse zone is 5 to 50 sec.

2. The process for producing the unsaturated nitrile according to claim 1, wherein a superficial gas velocity in the sparse zone is less than 1 m/s in the reaction step.

3. The process for producing the unsaturated nitrile according to claim 1, wherein an oxygen concentration in the reaction product gas discharged from the discharge port is 0.1 vol % or more in the reaction step.

4. The process for producing the unsaturated nitrile according to claim 1, wherein the oxygen concentration in the reaction product gas discharged from the discharge port is 0.1 vol % or more but 5.0 vol % or less in the reaction step.

5. The process for producing the unsaturated nitrile according to claim 1, wherein when the oxygen concentration in the reaction product gas discharged from the discharge port is less than 2.0 vol % in the reaction step, the relation of (the gas residence time)≤7.5×(the oxygen concentration)+30 is satisfied, and when the oxygen concentration in the reaction product gas discharged from the discharge port is 2.0 vol % or more in the reaction step, the relation of (the gas residence time)≤−3×(the oxygen concentration)+50 is satisfied.

6. The process for producing the unsaturated nitrile according to claim 1, wherein the hydrocarbon is propane and/or propylene.

* * * * *